(12) United States Patent
Dobrilovic (10) Patent No.: US 9,763,783 B2
(45) Date of Patent: Sep. 19, 2017

(54) PROSTHETIC DEVICE FOR HEART VALVE REINFORCEMENT AND REMODELING PROCEDURES

(71) Applicant: Nikola Dobrilovic, Providence, RI (US)

(72) Inventor: Nikola Dobrilovic, Providence, RI (US)

( * ) Notice: Subject to any disclaimer, the term of this patent is extended or adjusted under 35 U.S.C. 154(b) by 0 days.

(21) Appl. No.: 13/871,344

(22) Filed: Apr. 26, 2013

(65) Prior Publication Data
US 2013/0289720 A1 Oct. 31, 2013

Related U.S. Application Data

(60) Provisional application No. 61/639,482, filed on Apr. 27, 2012, provisional application No. 61/641,338, filed on May 2, 2012.

(51) Int. Cl.
*A61F 2/24* (2006.01)
(52) U.S. Cl.
CPC .................. *A61F 2/2445* (2013.01)
(58) Field of Classification Search
CPC ........ A61F 2/24; A61F 2/2409; A61F 2/2418; A61F 2/2427; A61F 2/2442; A61F 2/2445; A61F 2/2448
USPC ....................... 623/2.36–2.38, 2.41
See application file for complete search history.

(56) References Cited

U.S. PATENT DOCUMENTS

| | | |
|---|---|---|
| 5,071,431 A | 12/1991 | Sauter et al. |
| 5,360,014 A | 11/1994 | Sauter et al. |
| 5,489,296 A | 2/1996 | Love et al. |
| 5,669,919 A * | 9/1997 | Sanders et al. ............... 606/148 |
| 5,814,096 A | 9/1998 | Lam et al. |
| 5,843,177 A | 12/1998 | Vanney et al. |
| 6,019,739 A | 2/2000 | Rhee et al. |
| 6,110,200 A | 8/2000 | Hinnenkamp |
| 6,458,155 B1 | 10/2002 | Van Nguyen et al. |
| 6,678,962 B1 | 1/2004 | Love et al. |
| 6,702,763 B2 | 3/2004 | Murphy et al. |

(Continued)

FOREIGN PATENT DOCUMENTS

JP 11206739 A 8/1999

OTHER PUBLICATIONS

Peters Surgical, "uniRing Universal Annuloplasty System", 2007 http://www.zenomedical.com/Images/Products/Brochures/uniRing.pdf.

*Primary Examiner* — David Isabella
*Assistant Examiner* — Leslie Lopez
(74) *Attorney, Agent, or Firm* — Barlow, Josephs & Holmes, Ltd.

(57) ABSTRACT

A prosthetic heart valve reinforcement ring is disclosed. The prosthetic includes an outer ring sized and dimensioned to fit around an annulus of a heart valve and an inner ring configured and arranged to couple to the outer ring. The inner ring and the outer ring have complimentary mating formations configured and arranged to grip sutures therebetween. A method of reinforcing heart valve is also disclosed. Sutures are provided around an annulus of a heart valve. The sutures are corralled within an outer sizing ring. The outer sizing ring is placed around the annulus of the heart valve. An inner sizing ring is inserted within the outer ring, locking the sutures. The sutures are adjusted and the heart valve is tested for a proper fit. The outer sizing ring is removed and a prosthetic ring is placed over the inner sizing ring, locking the sutures. The sutures are tied.

11 Claims, 9 Drawing Sheets

(56) References Cited

U.S. PATENT DOCUMENTS

| | | | |
|---|---|---|---|
| 6,719,785 B2 | 4/2004 | Schoon et al. | |
| 7,338,484 B2 | 3/2008 | Schoon et al. | |
| 2002/0129820 A1* | 9/2002 | Ryan | A61F 2/2445 128/858 |
| 2003/0069593 A1* | 4/2003 | Tremulis et al. | 606/142 |
| 2008/0033544 A1 | 2/2008 | Lemmon | |
| 2009/0093877 A1* | 4/2009 | Keidar | A61F 2/2448 623/2.11 |
| 2009/0210051 A1* | 8/2009 | Camedda et al. | 623/2.36 |
| 2010/0030329 A1* | 2/2010 | Frater | A61F 2/2448 623/2.36 |
| 2010/0262043 A1 | 10/2010 | Sauter et al. | |
| 2012/0071968 A1 | 3/2012 | Li et al. | |

\* cited by examiner

PROSTHETIC DEVICE FOR HEART VALVE REINFORCEMENT AND REMODELING PROCEDURES

CROSS-REFERENCE TO RELATED APPLICATIONS

This patent document claims priority to earlier filed U.S. Provisional Patent Application Ser. No. 61/639,482, filed Apr. 27, 2012, and U.S. Provisional Patent Application Ser. No. 61/641,338, filed May 2, 2012, the entire contents of which are incorporated herein by reference.

BACKGROUND

1. Technical Field

The present patent document relates generally to heart valve ring and aortic root remodeling procedures, and more specifically to a prosthetic device for reinforcement of heart valves (mitral, tricuspid, aortic, pulmonic) and also for aortic root remodeling. With reference to the aortic root, the concept of sizing applies to not only the annulus, but also to the aortic root structure itself, both in terms of "ring" sizing, as well as, "graft" sizing (e.g. in Tirone David type procedures).

2. Background of the Related Art

Heart valve reinforcement rings (also, aortic root remodeling grafts) are difficult to size properly and, once sized properly, require additional labor to secure into position to the heart structure being reinforced or remodeled, as the case may be. This process can become technically even more difficult (more labor intensive) during minimally invasive procedures where the surgeon must implant the ring through a small incision under circumstances where even easy steps potentially become more difficult.

Therefore, there is a perceived need in the industry for heart valve annular rings (aortic root grafts) that are easier for a surgeon to secure into position especially in terms of proper sizing, ease of implantation, and minimization of surgical steps/operating time. These concepts may become even more relevant to patients undergoing minimally invasive procedures.

SUMMARY

The present invention solves the problems of the prior art by providing a heart valve ring (aortic root graft/composite ring with graft) that can be implanted with greater ease and accuracy. The ring includes an inner ring and an outer ring that snap together. Sutures are captured between the rings to allow the surgeon to test the fit of the ring. Once sure of the fit, the ring may be (permanently) secured into position in one of several ways. (Also the valve/root structures can be measured using disposable/reusable sizers, then swaped-out for the final prosthetic device to be permanently implanted). The ring may further include a composite graft, or simple graft, extending from the outer ring for aortic root remodeling procedures. Furthermore, the ring may be used with self-cinching or self-securing sutures.

BRIEF DESCRIPTION OF THE DRAWINGS

These and other features, aspects, and advantages of the present invention will become better understood with reference to the following description, appended claims, and accompanying drawings where:

DESCRIPTION OF THE PREFERRED EMBODIMENT

Provisional Patent Application Ser. Nos. 61/551,728, filed on Oct. 26, 2011, and 61/555,002, filed on Nov. 3, 2011, are incorporated herein by reference in their entirety.

The "sizing" component of the operation can be performed using a full set of separate sizers which can be reusable or disposable, such as is commonly the practice today for ring/valve surgery. Once the proper size has been determined (using the previously described sizing system), the actual prosthetic device can then be substituted and used for implantation. This type of system may have the added benefit of allowing for the final prosthesis to be constructed as a solid ring (no gap at 12 o'clock as seen in some figures of the sketches). Alternatively, the prosthesis itself can be used for both sizing and final implantation.

Though, the initial portion of the procedure involves two rings, the final prosthetic implant can either be the described combination of two rings, or alternatively, a single remaining ring, after one of the two rings is removed. This will depend on the method by which the prosthesis is secured into position.

Figure 1A:
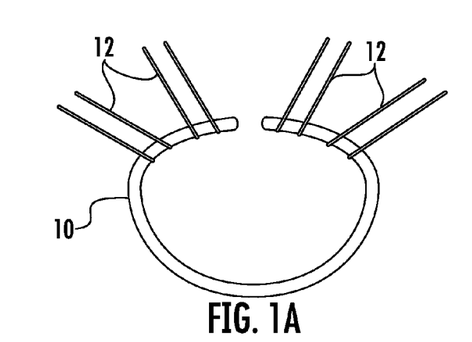
FIG. 1A shows a step of an outer portion of a sizing ring corralling the sutures around heart valve.
Figure 1B:
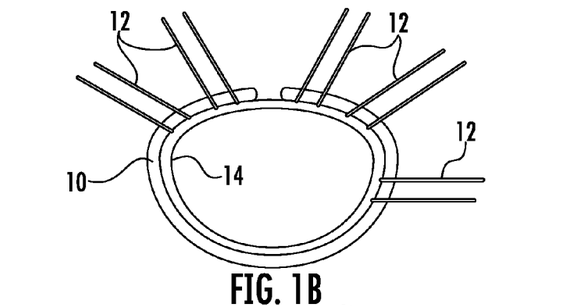
FIG. 1B shows a step of an inner portion of a sizing ring being inserted into the outer ring, trapping the sutures therebetween.
Figure 1C:
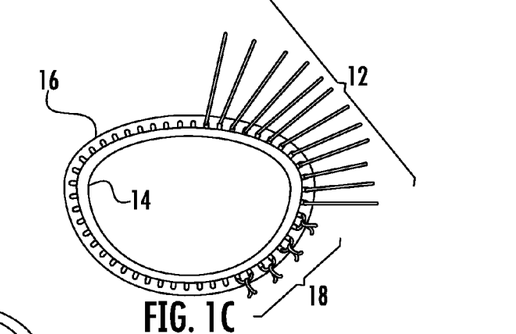
FIG. 1C shows a step of a prosthetic ring being substituted for the outer ring, with sutures being progressively tied to the prosthetic ring.
Figure 1D:
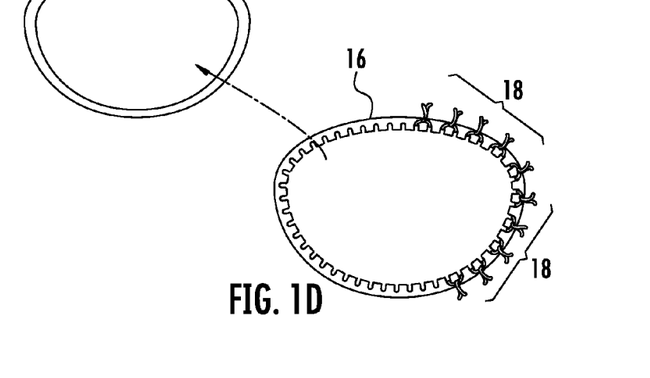
FIG. 1D shows a step of removing the inner sizing ring from the outer prosthetic ring.

The preferred embodiment results in the final implantation of only one of the two, paired rings. With this embodiment, the two ring system can be utilized such that the inner (inner or outer for aortic root) ring is a temporary guide used to help align and position sutures but is then removed after the sutures have been tied down onto the outer permanent ring (see, e.g., FIGS. 1D, 10C). Additional benefits to the one ring method include less prosthetic material. Also potential for infectious complications can be minimized because less or better material can be used (such as a plain metal ring instead of one covered with mesh to accept sutures).

Referring to FIGS. 1A-1D of the sketches demonstrates a quick summary of the process. 1A) Outer ring 10 of the sizing device is placed outside of the annular sutures 12. 1B) The inner ring 14 of the sizing device is combined with the outer ring 10, and the annular sutures 14 are captured in between. This combination can be repeated several times until the best size and shape have been selected. 1C) The outer sizing ring 10 is removed and replaced with the actual prosthetic device 16. The inner ring 14 can remain in place to help with retaining suture position and tying. Sutures 12 are tied down directly onto the prosthetic ring at 18. 1D) The inner ring 14 is removed, leaving the prosthetic ring 16 in place.

As will be more fully explained below, the sutures 12 can be tied without the use of additional needle passes by simply tying the "rings together." This is accomplished by "hooking" or "wrapping" the sutures 12 on elements of the prosthetic ring 16 such as barbs, posts, or some other form of either a groove or projection, etc., described in more detail below.

Figure 2A:
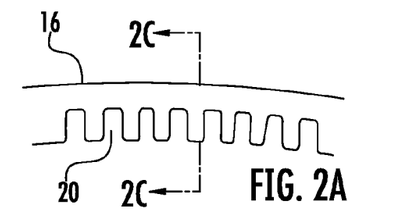
FIG. 2A shows a partial top view of a first embodiment of a suture engaging features of the prosthetic ring.

FIG. 2A shows spaced apart grooves 20 on the outer ring 16 of the prosthetic. In a cross-section view, FIG. 2C, the space between the grooves 20 includes a hook 22 formed within the body of the outer prosthetic ring 16. That is, a small recess 24 within the body of the outer ring 16 of the prosthetic is formed, creating a hooked end 26. The sutures 12 are tied off on the hook 22, preventing the outer ring 16 from moving on the annulus.

Figure 2B:
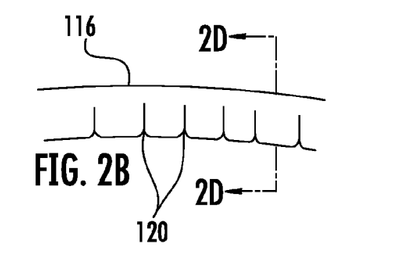
FIG. 2B shows a partial top view of a second embodiment of a suture engaging features of the prosthetic ring.
Figure 2C:
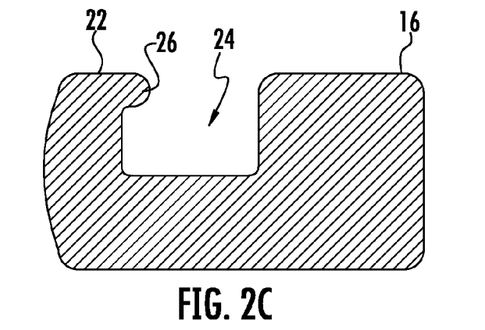
FIG. 2C is a cross-section view through line 2C-2C of FIG. 2A.
Figure 2D:
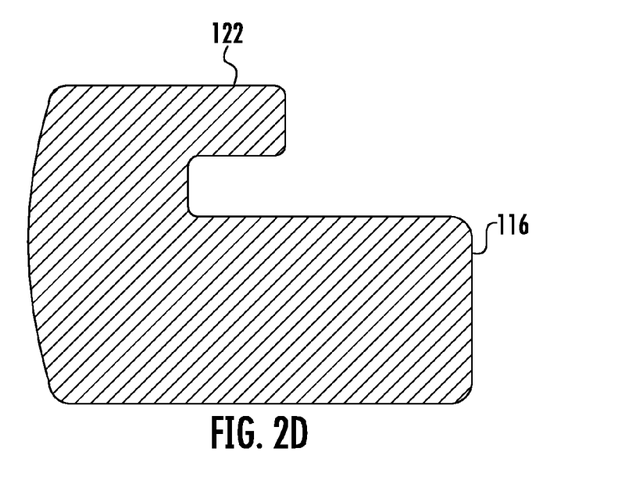
FIG. 2D is a cross-section view through line 2D-2D of FIG. 2B.

FIG. 2B shows an embodiment of the outer ring 116 where the outer ring 116 includes closely spaced grooves 120. The surfaces of the grooves may include a rubber coating to grip sutures. In a cross-section view, FIG. 2D, the space between the grooves 120 includes a hook 122 formed from a projection from the body of the outer ring 116. The sutures 12 are tied off on the hook 120, preventing the outer ring 116 from moving on the annulus.

One of various knot-tying devices can be used to tie, crimp, etc. the sutures 12 as is often done with minimally invasive surgical techniques.

Figures 3, 4:
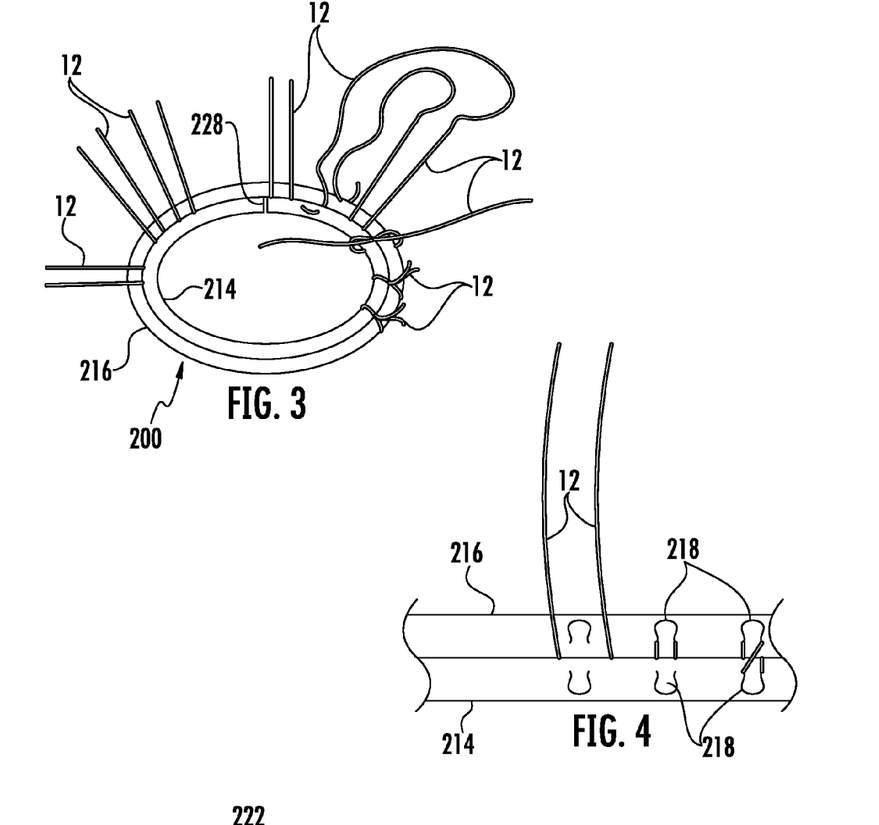
FIG. 3 shows a method of tying both the prosthetic and inner sizing ring to the surgical site.
FIG. 4 shows a partial view of a third embodiment of suture engaging features on both the prosthetic ring and the inner sizing ring.

Referring to FIG. 3, in a two-ring system, the prosthetic ring 200 includes an inner ring 214 with a gap 228, or defect, allowing sutures 12 to be gathered within the inner ring 214. The gap 228 also permits the inner ring 214 to flex inwardly. The inner ring 214 snap-fits into an outer ring 216. Together, the inner ring 214 and outer ring 216 may form a complete prosthesis. The inner ring 214 and outer ring 216 may include complimentary mating formations to permit a tight and secure fit together, yet permit the sutures 12 to be captured between the inner ring 214 and the outer ring 216. More specifically, the inner ring 214 may include a concave surface that complimentarily mates with a convex surface on the outer ring 216. The entire prosthesis 200 may then be tied down in place as is known in the art.

Because the embodiment includes an inner ring 214 and an outer ring 216 that can snap-fit around the sutures 12, the surgeon can determine an optimal fit for the prosthetic ring 200 prior to tying the prosthetic ring 200 in place around the annulus of the heart valve. The prosthetic ring 200 thus doubles as a sizer for determining the appropriate ring size for reinforcing the heart valve and then as the permanent prosthetic. The surgeon need not remove the prosthetic ring 200 once he has determined the fit is adequate. This prosthetic ring 200 may be used for any heart valve including aortic root remodeling procedures as well.

Figure 5:
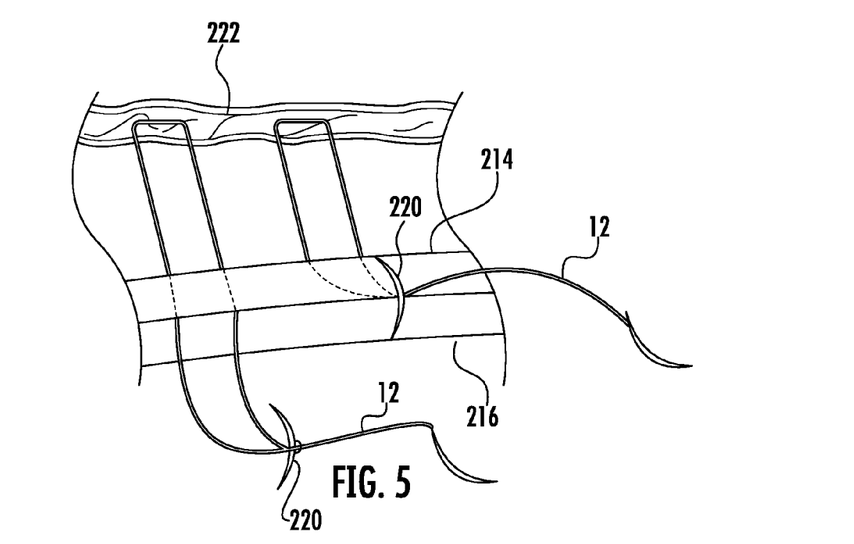
FIG. 5 shows a method of tying both the prosthetic and inner sizing ring to the sutures using a suture with a pre-tied clasp.

The inner ring 214 and the outer ring 216 may also include notches or stays 218 formed on the surface facing away from the mating surfaces of either ring (See, e.g. FIG. 4). These notches or stays 218 are configured to receive the suture 12 therein or tied thereto, respectively, and prevent the prosthetic ring 200 from shifting. Alternatively, a suture 12 with a self-tying knot and clasp 220 may be used to secure the assembled prosthetic ring 200 to the annulus 222 of the heart valve. (See, e.g., FIG. 5). Also, a suture tying hand tool may be used such as known in the art.

Figure 6A:
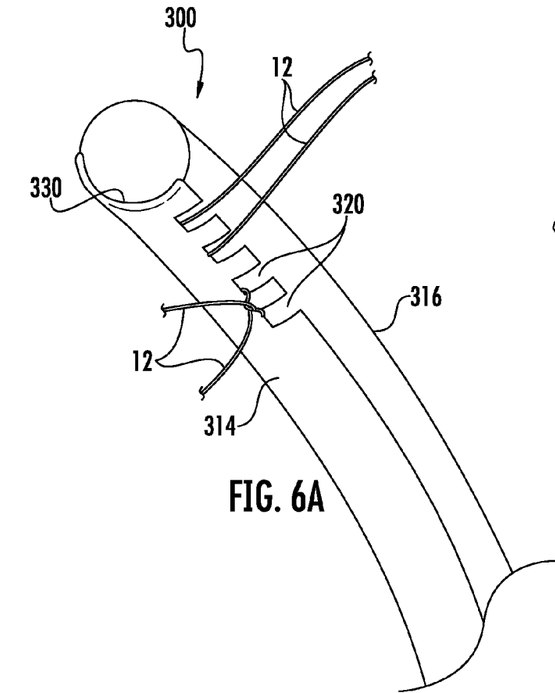
FIG. 6A shows a partial view another embodiment of the prosthetic having an outer ring and an inner ring, where only the inner ring includes suture engaging features.
Figure 6B:
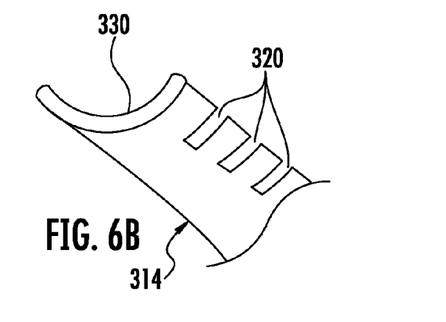
FIG. 6B shows a partial view of the inner ring shown in FIG. 6A in isolation.

Referring to FIGS. 6A and 6B, in another embodiment 300 of a two-ring system, the grooves 320 may be formed on the inner ring 314 instead of the outer ring 316. The inner ring 314 may also have a complimentary profile to the outer ring 316 thereby minimizing the overall size of the two rings 314, 316 when interlocked. More specifically, the inner ring 314 includes a concave outer surface 330 that complimentarily mates with a convex inner surface 332 of the outer ring 316. The grooves 320 formed on the inner ring 314 form tooth-like projections that the sutures 12 are tied down against. Additional sutures 12 may be wrapped around both rings 314, 316, securing the entire embodiment 300 to the annulus of the heart valve. The inner ring 314 may also include hooks and tie-down structures for the sutures 12 as described in FIGS. 2A, 2B and 4, and accompanying text.

Figure 7:
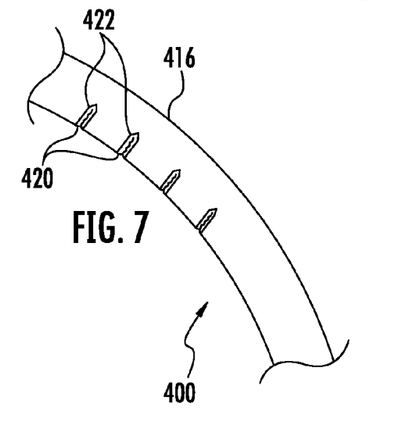
FIG. 7 shows a partial view of another embodiment where the prosthetic includes grooves coated with a soft suture-gripping material.

Referring to FIG. 7, in another embodiment 400, the grooves 420 on the outer prosthetic ring 416 may include a gripping material 422, such as a rubber coating, formed inside the grooves 420. The gripping material 422 allows the sutures 12 to be pulled into and out of the grooves 420 without fear of damage and to enable positioning and testing of the prosthetic ring 416. Once the fit is determined to be optimal, the sutures 12 may be tied down against the outer ring 416 as described previously. As may be appreciated by one skilled in the art, gripping material 422 may also be added to grooves 420 formed on an inner ring 320, as shown in FIGS. 6A and 6B, if used.

Figure 8:
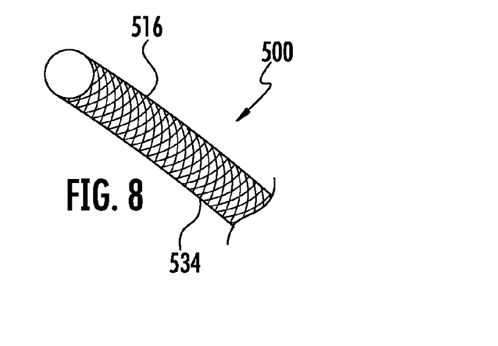
FIG. 8 shows a partial view of another embodiment of a prosthetic ring that includes a mesh sheath that the surgeon may sew directly to the surgical site.
Figures 9A, 9B:
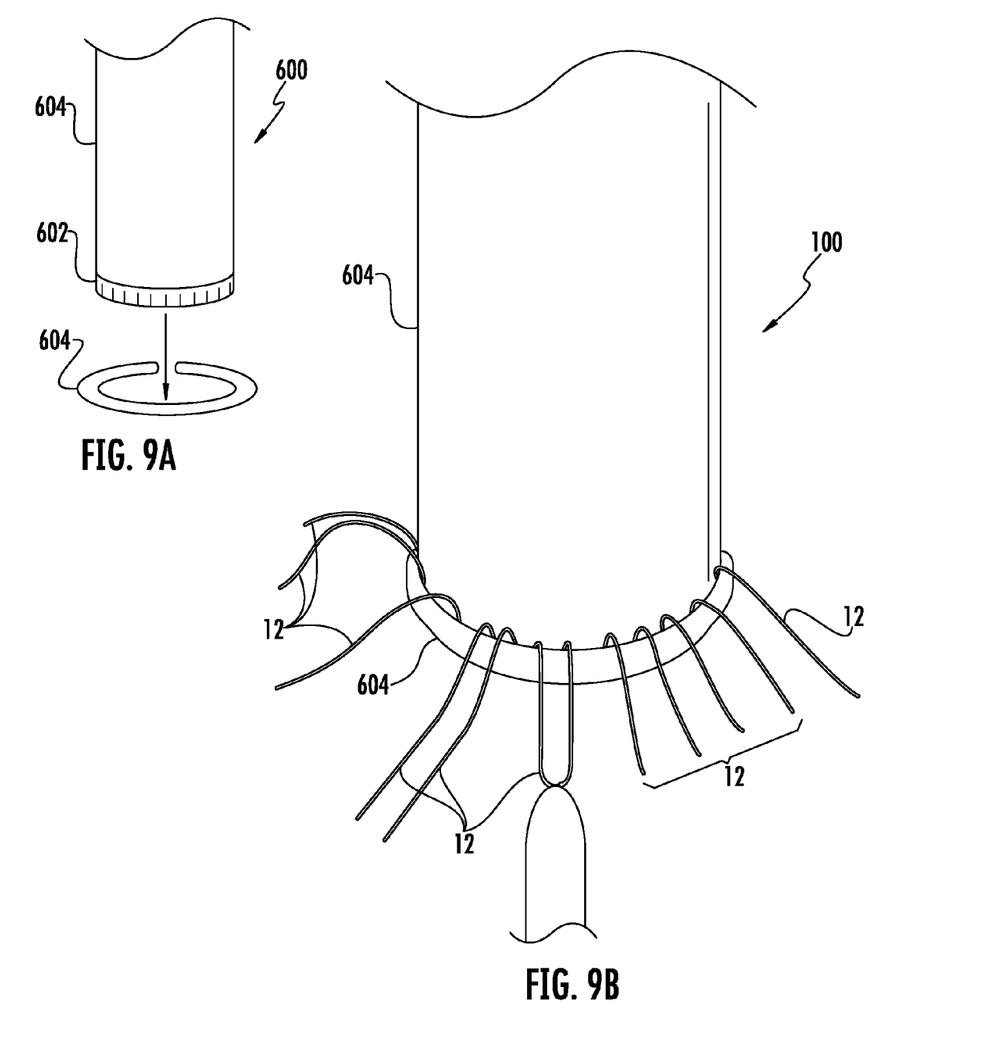
FIG. 9A shows an exploded partial view of an embodiment of a prosthetic ring with graft material extending therefrom.
FIG. 9B is a partial view of an embodiment of the prosthetic with graft material that locks inside an outer ring.
Figure 9C:
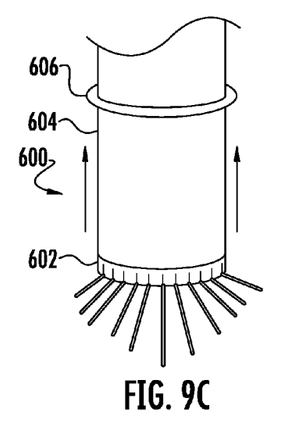
FIG. 9C is a partial view showing the outer ring being removed from the prosthetic ring with graft material.
Figure 9D:
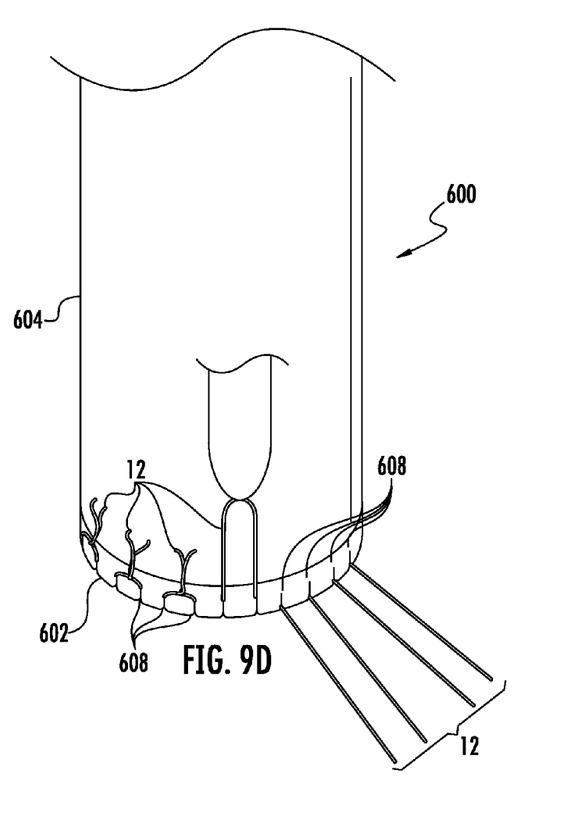
FIG. 9D is a partial view showing the prosthetic ring being tied in place at the surgical site.

Referring to FIG. 8, in another embodiment 500, the prosthetic ring 516 may also be sheathed in a mesh material 534, enabling a surgeon to sew the prosthetic ring 516 directly to the annulus. The mesh material 534 provides an additional method of anchoring the prosthetic ring 516 to the annulus where grooves and other tie-down structures described above, prove to be inadequate to create the fit the surgeon desires. By sewing through the mesh material 534, the surgeon may further secure the prosthetic ring 516 to achieve the most optimal fit.

Referring to FIGS. 9A-9D, 10A, 10B, and 11-13, similar concepts can be applied to remodeling of the aortic root of the heart. Various applications include, but are not limited to, annular reinforcement using a ring system, using a graft system, or a composite ring/graft system. Which can also be secured in a variety of ways as previously described, but in addition, a technique can be utilized where a ring is secured to the annulus and then the remaining composite ring/graft is snapped onto the first ring, etc.

Referring first to FIGS. 9A-9D, an embodiment 600 of a prosthetic ring 602 with graft material 604 extending therefrom is configured to interlock with a second outer ring 606. A second outer ring 606 may be used to facilitate sizing and tying of sutures 12 on the composite aortic root graft 600. The second outer ring 606 may then be removed once the composite aortic root graft 600 is implanted. The sutures 12 are captured between the outer ring 604 and prosthetic ring 602, enabling the surgeon to test for a proper fit. Once the fit is determined to be optimal, the composite aortic root graft 600 is tied in place.

The prosthetic ring 602 includes a number of suture engaging features 608, such as grooves, to permit the composite aortic root graft 600 to be secured in place. The grooves 608 may be formed on the bottom and outer surface of the prosthetic ring 602. Other suture engaging features described above in the other embodiments may also be used.

Figure 10A:
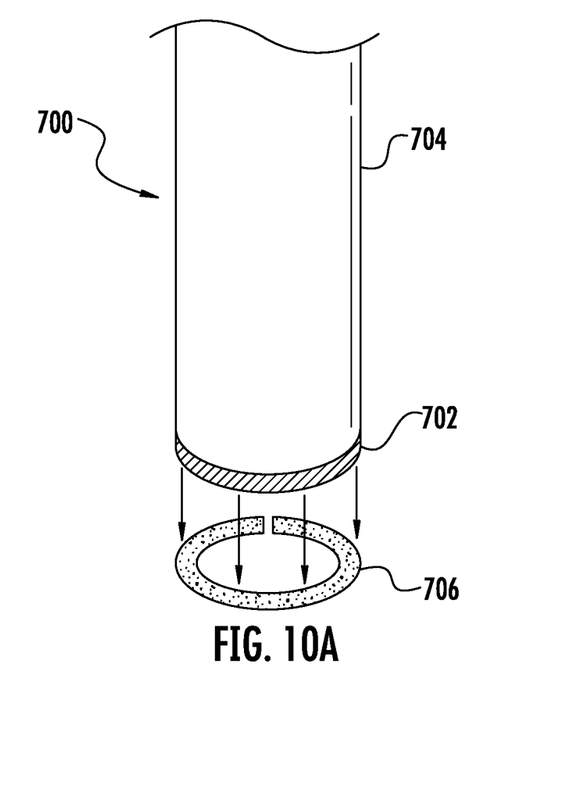
FIG. 10A is a partial exploded view of an embodiment of the prosthetic ring with graft material that snaps around or over an inner ring.
Figure 10B:
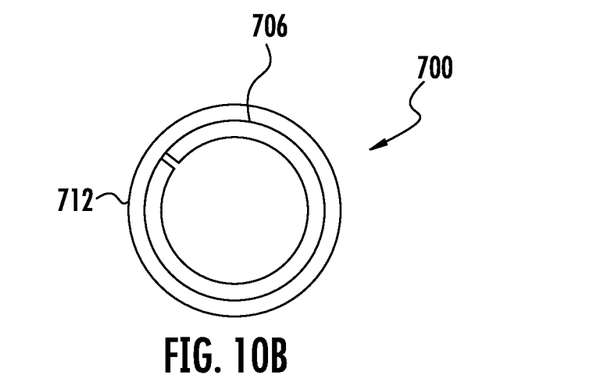
FIG. 10B is a bottom view of the embodiment shown in FIG. 10A, showing the outer ring locking around the inner ring.

Referring to FIGS. 10A and 10B, in another embodiment 700 with graft material 704 extending from the prosthetic ring 702, the prosthetic ring 702 locks around a second inner ring 706. In effect, this embodiment 700 is the reverse of the embodiment 600 shown in FIGS. 9A-9D.

Figure 11:
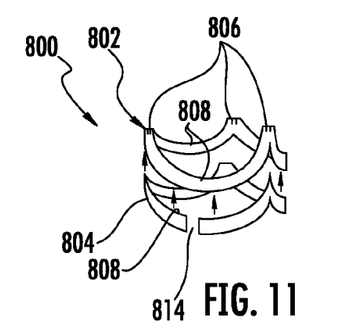
FIG. 11 is an exploded view of an embodiment of a prosthetic ring for aortic root remodeling procedures showing the peaks and valleys in the prosthetic ring.
Figure 12:
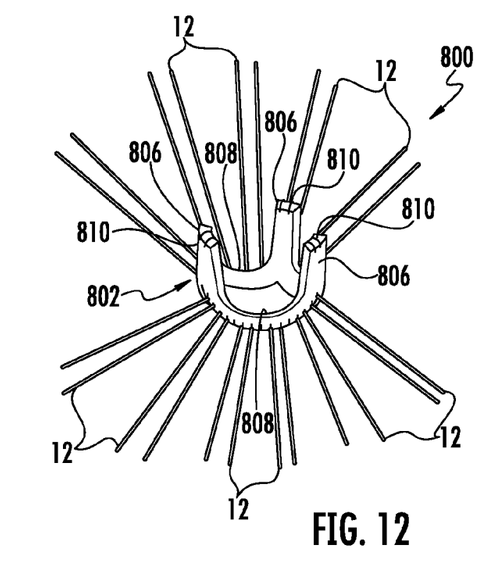
FIG. 12 is a perspective view of an embodiment of the prosthetic ring for aortic root remodeling procedures showing the sutures grasped in the prosthetic ring.
Figure 13:
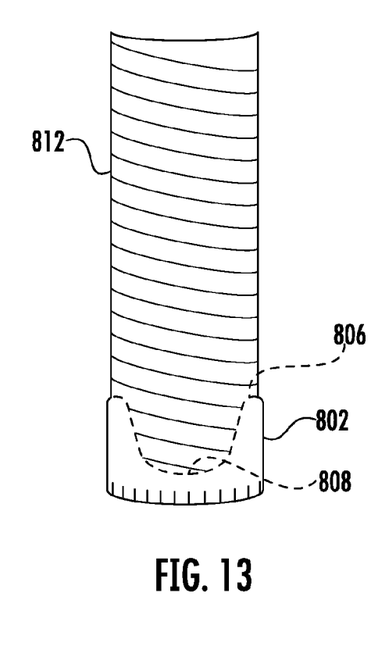
FIG. 13 is an elevation view of an embodiment of the prosthetic ring for aortic root remodeling procedures showing graft material extending from the prosthetic ring.

Referring to FIGS. 11-13, another embodiment of a prosthetic ring 800 for aortic root remodeling procedures is shown. The inner and outer rings 802, 804 of the prosthetic ring 800 of this embodiment includes peaks 806 and valleys 808 formed in the prosthetic ring 800 adapted to be fit around and suspend the aortic heart valve for aortic root remodeling procedures. Each peak 806 provides a point where the tab formed at the corner of the leaflets of the aortic valve may be supported and secured thereto. Grooves 810 may be provided to secure sutures 12 thereto, enabling temporary testing of the fit prior to sewing the sutures 12 in place. The inner and outer rings 802, 804 snap-fit together and may be secured in a like manner as described above for the other embodiments. The defect 814 (best seen in FIG. 11) to round up the sutures 12 and provide flexibility to the prosthetic ring 800 may be in the outer ring 802 instead of the inner ring 804.

The rigidity of the prosthetic ring 802 prevents undersizing as well as oversizing of the valve while tying sutures 12 down.

Referring to FIG. 13, graft material 812 may extend from the outer ring 802. Like the embodiment 700 shown in FIGS. 10A and 10B, the rings 802, 804 may be reversed, where the graft material 812 extends from the inner ring 804 instead. The graft material 812 may be secured in place to the aortic walls to further stabilize the aorta as is known in the art.

In addition, a stand-alone prosthetic ring 800 may be secured around the aortic valve and graft material attached to the aorta and heart tissues separately.

Figure 14:
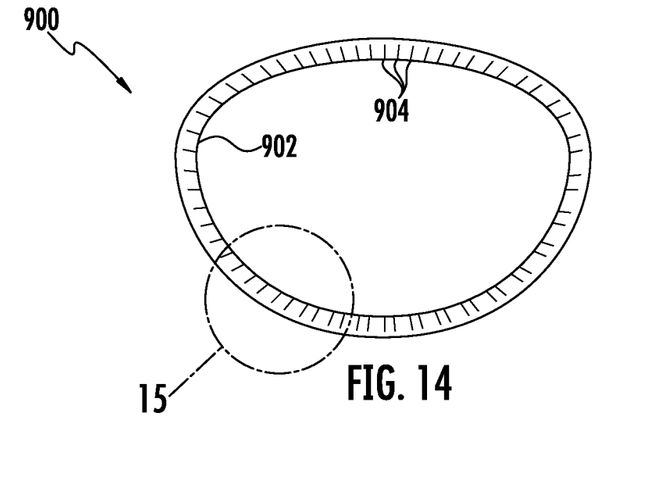
FIG. 14 is a view of a single ring system, prosthetic heart valve ring, showing a plurality of groove with suture gripping material.
Figure 15:
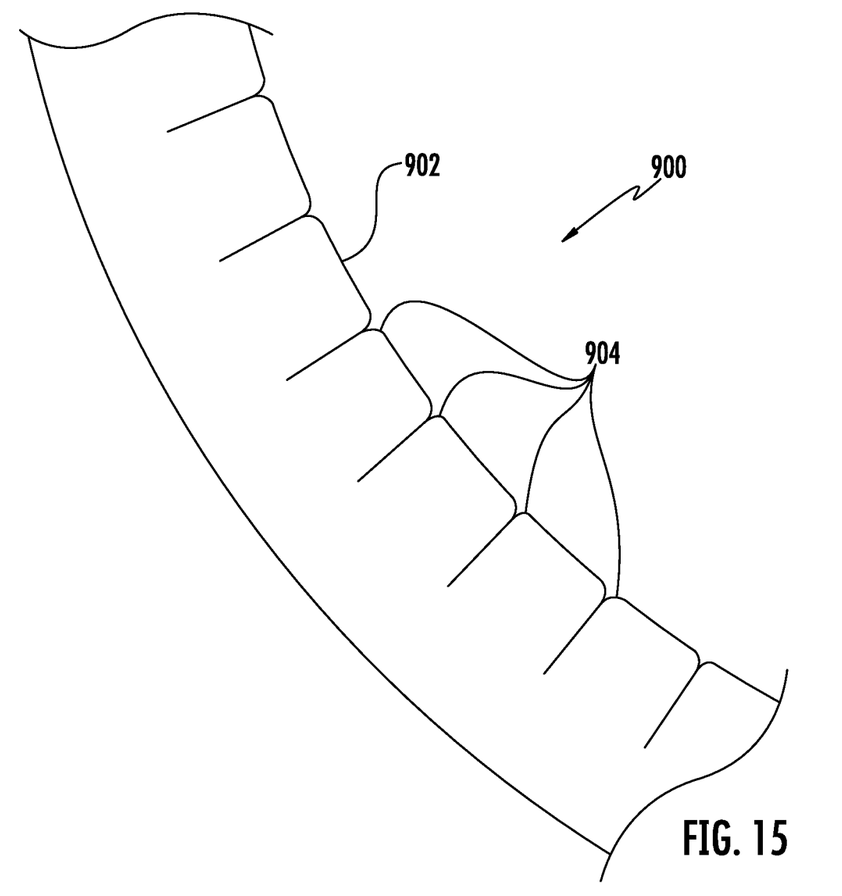
FIG. 15 is an enlarged view of inset 15 of FIG. 14.

Referring to FIGS. 14 and 15, alternatively, the sizer and prosthesis 900 can function each as an independent one-ring system. On the inner surface 902 of the ring 900 are a number of grooves 904 to secure the sutures. The grooves 904 themselves provide a firm but gentle grasping upon the sutures (rubber coating, etc.) much like the function performed by a valve or suture organizer. As such, the sutures can easily be moved from groove 904 to groove 904 until optimal spacing is achieved. Sutures can then be tied down in this optimal position. Sizers can be swapped out as needed before selecting the final ring prosthesis 900. In the case of flexible or partial rings they can be attached to a rigid temporary support structure which can be cut out/away once the prosthesis 900 has been tied down. The sizer/prosthesis 900 itself can also function as the suture or valve organizer.

It would be appreciated by those skilled in the art that various changes and modifications can be made to the illustrated embodiments without departing from the spirit of the present invention. All such modifications and changes are intended to be within the scope of the present invention, except insofar as limited by the appended claims.

I claim:

1. A method of reinforcing a heart valve, comprising:
providing annular sutures sutured to an annulus of the heart valve;
corralling the annular sutures within an outer sizing ring;
after the annular sutures have been corralled, placing the outer sizing ring around the annulus of the heart valve;
inserting an inner sizing ring within the outer sizing ring, temporarily locking the annular sutures radially between the outer sizing ring and the inner sizing ring;
during insertion of the inner sizing ring within the outer sizing ring contemporaneously adjusting the annular sutures to achieve a corrected fit of leaflets of the heart valve;
testing the corrected fit of the leaflets after the annular sutures have been adjusted;
after the corrected fit of the leaflets has been determined, replacing the outer sizing ring with a prosthetic ring over the inner sizing ring-thereby locking the annular sutures between the prosthetic ring and the inner sizing ring; and
tying the annular sutures.

2. The method of claim 1, further comprising removing the inner sizing ring.

3. The method of claim 2, wherein the inner sizing ring is removed after the annular sutures are tied.

4. The method of claim 1, further comprising tying the annular sutures to the prosthetic ring.

5. The method of claim 1, further comprising tying the annular sutures to both the inner sizing ring and the prosthetic ring.

6. The method of claim 1, further comprising using a knot-tying device to tie the annular sutures in the tying the annular sutures step.

7. The method of claim 1, further comprising wrapping the annular sutures around the prosthetic ring.

8. The method of claim 1, further comprising suturing the annular sutures through graft material extending from the prosthetic ring.

9. The method of claim 1, further comprising suspending tabs of tissue where leaflets meet to peaks formed in the prosthetic ring.

10. The method of claim 1, further comprising repeating the steps of adjusting the annular sutures and testing the heart valve until the corrected fit of the leaflets is achieved.

11. The method of claim 1, further comprising testing the heart valve for the corrected fit of the leaflets after the outer sizing ring is replaced with the prosthetic ring.

* * * * *